(12) United States Patent
Gai et al.

(10) Patent No.: US 12,097,224 B2
(45) Date of Patent: Sep. 24, 2024

(54) **USE OF CELL WALL SKELETON OF ISOLATED *RHODOCOCCUS RUBER* FOR PREPARING HUMAN PAPILLOMA VIRUS INFECTION TREATMENT DRUG**

(71) Applicant: LIAONING GREATEST BIO-PHARMACEUTICAL CO. LTD., Benxi (CN)

(72) Inventors: Bo Gai, Benxi (CN); Chunyan Dou, Benxi (CN); Yi Zhang, Benxi (CN); Guoying Zhang, Benxi (CN)

(73) Assignee: Liaoning Greatest Bio-Pharmaceutical Co., Ltd., Benxi (CN)

( * ) Notice: Subject to any disclaimer, the term of this patent is extended or adjusted under 35 U.S.C. 154(b) by 638 days.

(21) Appl. No.: 17/421,718

(22) PCT Filed: Dec. 24, 2019

(86) PCT No.: PCT/CN2019/127895
§ 371 (c)(1),
(2) Date: Jul. 8, 2021

(87) PCT Pub. No.: WO2020/147530
PCT Pub. Date: Jul. 23, 2020

(65) Prior Publication Data
US 2022/0265729 A1  Aug. 25, 2022

(30) Foreign Application Priority Data

Jan. 15, 2019 (CN) .......................... 201910036001.4
Oct. 25, 2019 (CN) ......................... 201911022193.X

(51) Int. Cl.
| | | |
|---|---|---|
| A61K 35/74 | (2015.01) | |
| A61K 9/00 | (2006.01) | |
| A61P 17/02 | (2006.01) | |
| A61P 31/20 | (2006.01) | |
| C12N 1/20 | (2006.01) | |
| C12R 1/01 | (2006.01) | |

(52) U.S. Cl.
CPC ............ *A61K 35/74* (2013.01); *A61K 9/0014* (2013.01); *A61P 17/02* (2018.01); *A61P 31/20* (2018.01); *C12N 1/205* (2021.05); *C12R 2001/01* (2021.05)

(58) Field of Classification Search
None
See application file for complete search history.

(56) References Cited

U.S. PATENT DOCUMENTS

2009/0028973 A1* 1/2009 Zhang .................... A61P 31/20
424/780
2015/0245997 A1  9/2015 Harashima et al.

FOREIGN PATENT DOCUMENTS

| CN | 1519312 A | 8/2004 |
|---|---|---|
| CN | 1735431 A | 2/2006 |
| CN | 101033454 A | 9/2007 |
| CN | 101250490 A | 8/2008 |
| CN | 101323865 A | 12/2008 |
| CN | 101580808 A | 11/2009 |
| CN | 101619299 A | 1/2010 |
| CN | 102250796 A | 11/2011 |
| CN | 102604875 A | 7/2012 |
| CN | 103160491 A | 6/2013 |
| CN | 103509833 A | 1/2014 |
| CN | 103627653 A | 3/2014 |
| CN | 104830738 A | 8/2015 |
| CN | 105820982 A | 8/2016 |
| CN | 10643446 A | 2/2017 |
| CN | 106591168 A | 4/2017 |
| CN | 106591172 A | 4/2017 |
| CN | 107151635 A | 9/2017 |
| CN | 108130288 A | 6/2018 |
| CN | 108862590 A | 11/2018 |
| CN | 109576180 A | 4/2019 |
| CN | 109666609 A | 4/2019 |
| WO | 2007/071982 A1 | 6/2007 |

OTHER PUBLICATIONS

Sutcliffe, Iain C. "Cell envelope composition and organisation in the genus *Rhodococcus*." Antonie Van Leeuwenhoek 74 (1998): 49-58. (Year: 1998).*
Xin, Fan et al., "Whole-genome sequencing and expression analysis of heat shock protein DnaK from *Rhodococcus ruber* SD3", Genomics and Applied Biology, pp. 1-13, English abstract only (Jan. 2019).
Hua, Gougen et al., "The taxonomy and application of *Rhodococcus*", Microbiology China, 30(4):107-111, English abstract only (2003).
Hu, Songqing et al., "Modern technology of particle size measurement", Modern Chemical Industry, 22(1):58-61, English abstract only (2002).
Zhu, Guanping et al., "Immunological properties of CWS from BCG and *Rhodococcus corallina*", Chinese Journal of Antibiotics No. 3, (Dec. 31, 1984).
Li, H. et al., "In vitro and in vivo anticancer activity of sophorolipids to human cervical cancer", Applied Biochemistry and Biotechnology, 181:1372-1387 (Dec. 31, 2017).

\* cited by examiner

*Primary Examiner* — Robert J Yamasaki
*Assistant Examiner* — Charles Zoltan Constantine
(74) *Attorney, Agent, or Firm* — Rodney J. Fuller; BOOTH UDALL FULLER, PLC

(57) ABSTRACT

Disclosed is a use of a cell wall skeleton of isolated *Rhodococcus ruber* or a composition containing the same for preparing a human papillomavirus infection treatment drug. The cell wall skeleton of *Rhodococcus ruber* isolated from *Rhodococcus ruber* was stored and preserved at China General Microbiological Culture Collection Center, No. 1, West Beichen Road, Chaoyang District, Beijing on Mar. 22, 2019 with accession number CGMCC 17431.

9 Claims, 1 Drawing Sheet

Figure 1

```
GGTTAGGCCACCGGCTTCGGGTGTTACCGACTTTCATGACGTGACGGGCGGTGTGTACAAGGCCCGGGAACGTATTCACCGCA
GCGTTGCTGATCTGCGATTACTAGCGACTCCGACTTCACGGGGTCGAGTTGCAGACCCCGATCCGAACTGAGACCGGCTTTAA
GGGATTCGCTCCACCTCGCGGTATCGCAGCCCTCTGTACCGGCCATTGTAGCATGTGTGAAGCCCTGGACATAAGGGGCATGA
TGACTTGACGTCGTCCCCACCTTCCTCCGAGTTGACCCCGGCAGTCTCCTGCGAGTCCCCACCATTACGTGCTGGCAACACAG
GACAAGGGTTGCGCTCGTTGCGGGACTTAACCCAACATCTCACGACACGAGCTGACGACAGCCATGCACCACCTGTACACCGA
CCACAAGGGAAACCCCATCTCTGGGGCGGTCCGGTGTATGTCAAACCCAGGTAACGTTCTTCGCGTTGCATCGAATTAATCCA
CATGCTCCGCCGCTTGTGCGGGCCCCGTCAATTCCTTTGAGTTTTAGCCTTGCGGCCGTACTCCCCAGGCGGGGCGCTTAAT
GCGTTAGCTACGGCACGGATCCCGTGGAAGGAAACCCACACCTAGCGCCCACCGTTTACGGCGTGGACTACCAGGGTATCTAA
TCCTGTTCGCTACCCACGCTTTCGCTCCTCAGCGTCAGTTACTGCCCAGAGACCCGCCTTCGCCACCGGTGTTCCTCCTGATA
TCTGCGCATTTCACCGCTACACCAGGAATTCCAGTCTCCCCTGCAGTACTCAAGTCTGCCCGTATCGCCTGCAAGCCCGCAGT
TGAGCTGCGGGTTTTCACAGACGACGCGACAAACCGCCTACGAGCTCTTTACGCCCAGTAATTCCGGACAACGCTCGCACCCT
ACGTATTACCGCGGCTGCTGGCACGTAGTTGGCCGGTGCTTCTTCTGTACCTACCGTCACTTGCGCTTCGTCGGTACTGAAAG
AGGTTTACAACCCGAAGGCCGTCATCCCTCACGCGGCGTCGCTGCATCAGGCTTGCGCCCATTGTGCAATATTCCCCACTGCT
GCCTCCCGTAGGAGTCTGGGCCGTGTCTCAGTCCCAGTGTGGCCGGTCGCCCTCTCAGGCGGCTACCCGTCGTCGCCTTGGT
GGGCCGTTACCCCACCAACAAGCTGATAGGCCGCGGGCCCATCCTGCACCGGAAAACCTTTCCACCCCGGAACATGCATCCCG
AGGTCCTATCCGGTATTAGACCCAGTTTCCCAGGCTTATCCCGAAGTGCAGGGCAGATCACCCACGTGTTACTCACCCGTTCG
CCACTAATCCACCCAGCAAGCTGGCTTCATCGTTCGAC
```

Figure 2

USE OF CELL WALL SKELETON OF ISOLATED *RHODOCOCCUS RUBER* FOR PREPARING HUMAN PAPILLOMA VIRUS INFECTION TREATMENT DRUG

CROSS REFERENCE TO RELATED APPLICATIONS

This application is the U.S. National Stage of International Application No. PCT/CN2019/127895, filed on Dec. 24, 2019, which claims the priority of Chinese patent application "*Rhodococcus ruber* cell wall skeleton and use thereof" filed on Jan. 15, 2019 (application No. 201910036001.4) and of Chinese patent application "An isolated *Rhodococcus ruber*" filed on Oct. 25, 2019 (application No. 201911022193.X), and their entire contents of which are incorporated herein by reference.

Biological Deposit of *Rhodococcus Ruber* Accession No. 17431

A Biological Deposit of *Rhodococcus Ruber* Accession No. 17431 was made at the China General Microbiological Culture Collection Center (CGMCC) (Yard No. 1(3) West Beichen Road, Chaoyang District, Beijing, Institute of Microbiology, Chinese Academy of Sciences; postal code: 100101), on Mar. 22, 2019, under the provisions of the Budapest Treaty, and assigned by the International Depositary Authority the accession number 17431. Upon issuance of a patent, all restrictions upon the Deposit will be irrevocably removed, and the Deposit is intended to meet the requirements of 37 CFR §§ 1.801-1.809. The Deposit will be maintained in the depository for a period of 30 years, or 5 years after the last request, or for the effective, enforceable life of the patent, whichever is longer, and will be replaced, if necessary, during that period; and the requirements of 37 CFR §§ 1.801-1.809 are met.

FIELD OF THE INVENTION

The present disclosure relates to the fields of medicine, microbiology and biopharmacy. Specifically, the present invention relates to use of an isolated *Rhodococcus ruber* cell wall skeleton and a pharmaceutical composition comprising the same in preparing a medicament for treating human papilloma virus infection.

BACKGROUND OF THE INVENTION

Human papilloma virus (HPV) is a kind of spherical DNA viruses with high specificity for epithelium, which only infects human skin and mucosa, and can cause squamous epithelial hyperplasia in human skin and mucosa to form papilloma.

At present, more than 130 HPV subtypes have been isolated. Different types of HPV cause different clinical manifestations, which are divided into skin type and mucosa type according to the site of the epithelium infected; and different types of HPV are also divided into high-risk type and low-risk type according to the different degrees of risks of causing tumors. Skin low-risk HPV is related to common warts, flat warts, toe warts, etc.; skin high-risk HPV can cause vulvar cancer, penile cancer, anal cancer, prostate cancer, bladder cancer, etc. Mucosa low-risk HPV can infect genitals, anus, oropharynx and esophageal mucosa; mucosa high-risk HPV can cause cervical cancer, rectal cancer, oral cancer, tonsil cancer, etc. About 35 types are related to genital tract infections, and about 20 types are related to tumors. For example, low-risk HPV types include: HPV 6, 11, 42, 43, 44, CP8304, etc., which can cause benign lesions such as genital condyloma, including low-grade cervical intraepithelial neoplasia (CINI). High-risk HPV types include: HPV16, 18, 31, 33, 35, 45, 51, 52, 56, 58, 59, 68, etc., which can cause high-grade cervical intraepithelial neoplasia (CINII, CINIII) and cervical cancer, and the most common HPV subtypes involved in cervical cancer are type 16 and type 18.

HPV infection is one of the most common sexually transmitted diseases in the world and is related to sexual behavior. In particular, persistent high-risk HPV infection is the primary cause of cervical cancer, which has been recognized in the world. Therefore, human papilloma virus infection seriously endangers human health and even life.

There are approximately 10%-15% of new infections in women worldwide each year. In most countries, HPV infection is very common. Young sexually active women have the highest HPV infection rate, and the infection peaks between the ages of 18-28. The HPV infection period is relatively short for most women, and the infection usually disappears in about 8-10 months. However, 10%-15% of women over the age of 35 still have persistent infections. These women with persistent HPV infections then become a high-risk population for cervical cancer.

Statistics from the World Health Organization show that cervical cancer ranks second in the global mortality rate of women from cancer, and even ranks first in some developing countries. Every year, there are 500,000 new cases of cervical cancer worldwide, and about 200,000 people die from cervical cancer, 80% of which occur in developing countries. Cervical cancer accounts for 24% of malignant tumors in women in developing countries and 7% in developed countries. In the $21^{st}$ century, cervical cancer is becoming one of the major diseases affecting the health of women worldwide.

According to incomplete statistics, there are currently about 138,000 patients with cervical cancer in China, and about 50,000 people die from cervical cancer each year, accounting for a quarter of the total number of new cervical cancer cases in the world. But what troubles the experts is that, due to the imperfect early screening work, in a large number of patients, cervical cancer is often found in the late stage, and they lose the valuable opportunity of early treatment. Moreover, there is now a trend of having cervical cancer in younger patients.

Prevention and Treatment of HPV Infection

Prevention of HPV infection: preventing premature sex, avoiding unclean sex, reducing cross-infection, quitting smoking and alcohol, etc., adopting a healthy lifestyle, strengthening the immunity of the body, and vaccinating the preventive HPV vaccine at an appropriate age, which can reduce the infection risk of the HPV types included in the vaccine.

Currently, there is no effective anti-HPV infection drug. The FDA has approved three vaccines to prevent HPV infection, namely bivalent vaccine, quadrivalent vaccine and nine-valent vaccine, respectively. These vaccines can effectively prevent infections of some HPV types, but preventive vaccines have no effect on HPV infections that have already been identified or lesions caused by HPV. Therefore, there is an eager need in the field for more effective and safer new drugs to eliminate HPV infection.

*Rhodococcus ruber* is a gram-positive bacterium. Generally speaking, its colony is orange-yellow or orange-red in color, and round in shape; the size of the colony is about 1 mm to 2 mm; the cell morphology is spherical or short rod-shaped; it can form primary branched mycelium; and it has no flagella. *Rhodococcus ruber* is aerobic and chemically heterotrophic.

At present, researchers have performed whole gene sequencing of *Rhodococcus ruber*. For example, Fan Xin et al. sequenced the whole genome of *Rhodococcus ruber* SD3 strain and performed bioinformatic analysis. The whole genome length of the SD3 strain is about 5.37 Mb, the GC content is about 70.63%, and the GenBank accession number is CP029146 (Fan Xin, Whole-genome sequencing and expression analysis of heat shock protein DnaK from *Rhodococcus ruber* SD3, Genomics and Applied Biology, January 2019).

The *Rhodococcus* genus can adapt to a variety of living environments due to its strong tolerance to organic matters and its wide degradation spectrum. Therefore, *Rhodococcus* is widely used in the fields of pollution remediation, organic compound degradation, sewage treatment, etc. At present, the main application field of *Rhodococcus ruber* lies in environmental management, see CN108862590A, CN107151635A, CN102250796A, CN1519312A, CN103627653A, CN101033454A, CN108130288A, CN104830738A, CN101619299A, CN103509833A, CN106434466A, CN101580808A, CN102604875A, CN103160491A, CN106591168A, CN106591172A and CN105820982A.

CN109576180A discloses a bacterium RDC-01 screened from the red soil in the suburbs near Panyu District, Guangzhou. After 16S rRNA gene sequence analysis and culture characteristics identification, the strain was identified as *Rhodococcus ruber*. After inactivation, the bacterium was added as an immune adjuvant to an inactivated vaccine for animals, and was found to be able to promote the production of antibodies in animals.

However, the application of *Rhodococcus ruber* in the field of human medicine has not yet been reported. The inventors have unexpectedly discovered the beneficial uses of *Rhodococcus ruber* cell wall skeleton and the composition containing the same in treating human papilloma virus (HPV) infection.

SUMMARY OF THE INVENTION

According to some embodiments of the present disclosure, in one aspect, an isolated *Rhodococcus ruber* is provided.

According to some specific embodiments of the present disclosure, a *Rhodococcus ruber* is provided, which was deposited at China General Microbiological Culture Collection Center (CGMCC) on Mar. 22, 2019 (No. 1-3 West Beichen Road, Chaoyang District, Beijing, Institute of Microbiology, Chinese Academy of Sciences; zip code: 100101), under deposit number CGMCC 17431. The deposit meets the requirements of the Budapest Treaty on the International Recognition of the Deposit of Microorganisms for the Purposes of Patent Procedure.

According to some embodiments of the present disclosure, a *Rhodococcus ruber* and derivative products thereof are provided. The derivative products are derived from the *Rhodococcus ruber* and comprise the components of the *Rhodococcus ruber* (such as proteins, nucleic acids, lipids, cell walls and components thereof, carbohydrates and metabolites).

In specific embodiments, an isolated *Rhodococcus ruber* cell wall is provided.

In specific embodiments, an isolated *Rhodococcus ruber* cell wall is provided, the *Rhodococcus ruber* referring to the strain with the deposit number CGMCC 17431.

In specific embodiments, an isolated *Rhodococcus ruber* cell wall skeleton is provided.

In specific embodiments, an isolated *Rhodococcus ruber* cell wall skeleton is provided, the *Rhodococcus ruber* referring to the strain with the deposit number CGMCC 17431.

According to some embodiments of the present disclosure, a pharmaceutical composition is provided, which comprises the *Rhodococcus ruber* cell wall or the *Rhodococcus ruber* cell wall skeleton according to the present disclosure.

According to some embodiments of the present disclosure, a product derived from *Rhodococcus ruber* is provided, which comprises a product obtained by disrupting the *Rhodococcus ruber*.

According to some other embodiments of the present disclosure, a product derived from *Rhodococcus ruber* is provided, which comprises a product obtained by disrupting and purifying (removing lipids, nucleic acids and proteins from) the *Rhodococcus ruber*.

According to some other embodiments of the present disclosure, a product derived from *Rhodococcus ruber* is provided, which comprises *Rhodococcus ruber* cell wall.

According to some other embodiments of the present disclosure, a product derived from *Rhodococcus ruber* provided, which comprises *Rhodococcus ruber* cell wall skeleton.

According to some embodiments of the present disclosure, a pharmaceutical composition or a medical apparatus is provided, which comprises a product obtained by disrupting the *Rhodococcus ruber*.

According to some other embodiments of the present disclosure, a pharmaceutical composition or a medical apparatus is provided, which comprises a product obtained by disrupting and purifying (removing lipids, and/or nucleic acids, and/or proteins from) the *Rhodococcus ruber*.

According to some other embodiments of the present disclosure, a pharmaceutical composition or a medical apparatus is provided, which comprises the *Rhodococcus ruber* cell wall.

According to some other embodiments of the present disclosure, a pharmaceutical composition or a medical apparatus is provided, which comprises the *Rhodococcus ruber* cell wall skeleton.

According to some other embodiments of the present disclosure, a pharmaceutical composition or a medical apparatus is provided, which comprises the product derived from *Rhodococcus ruber* as described above.

In specific embodiments, the pharmaceutical composition further comprises a pharmaceutically acceptable excipient.

In some embodiments, in the pharmaceutical composition, the product derived from *Rhodococcus ruber* is in 1 part by weight, and the pharmaceutically acceptable excipient is in 200 to 300 parts by weight (for example, in 200, 210, 220, 230, 240, 250, 260, 270, 280, 290, or 300 parts by weight, or any point value within any two numerical ranges).

In some other embodiments, in the pharmaceutical composition, the *Rhodococcus ruber* cell wall is in 1 part by weight, and the pharmaceutically acceptable excipient is in 200 to 300 parts by weight (for example, in 200, 210, 220, 230, 240, 250, 260, 270, 280, 290 or 300 parts by weight, or any point value within any two numerical ranges).

In still other embodiments, in the pharmaceutical composition, the *Rhodococcus ruber* cell wall skeleton is in 1 part by weight, and the pharmaceutically acceptable excipient is in 200 to 300 parts by weight (for example, in 200, 210, 220, 230, 240, 250, 260, 270, 280, 290 or 300 parts by weight, or any point value within any two numerical ranges).

In some embodiments, the pharmaceutical composition can be prepared as a liquid (liquid formulation).

In some other embodiments, the pharmaceutical composition can be prepared as a solid (dry powder formulation or lyophilized powder formulation).

The skilled person understands that, for the pharmaceutical composition of the present disclosure, the liquid formulation and the dry powder formulation (or lyophilized powder formulation) can be converted into each other, and the difference lies only in the water content. A dry powder formulation (or lyophilized powder formulation) is obtained by removing most or all of the water from the liquid formulation. A liquid formulation is obtained by dissolving (or reconstituting) the dry powder formulation (or lyophilized powder formulation).

In some embodiments, the medicament or the pharmaceutical composition is prepared into a dosage form selected from the group consisting of ointment, cream, gel, lotion, tincture, liniment, oil, paste, aerosol, buccal tablet, patch, lyophilized powder and suspension.

In some embodiments, the dosage form is a buccal tablet. For example, it can be prepared by pressing the lyophilized powder.

In some embodiments, the pharmaceutically acceptable excipient relates to, but is not limited to: filler, stabilizer, flavoring agent, disintegrant, binder and lubricant.

According to some embodiments of the present disclosure, a method for the preparation of a product derived from *Rhodococcus rubers* is provided, which comprises or consists of the following steps:
1) providing *Rhodococcus ruber*;
2) culturing said *Rhodococcus ruber*;
3) collecting the cultured *Rhodococcus ruber*;
4) disrupting the cultured *Rhodococcus ruber* to obtain a disrupted product;
5.1) performing the operation of removing lipids from the disrupted product;
5.2) performing the operation of removing nucleic acids from the disrupted product;
5.3) performing the operation of removing proteins from the disrupted product;
5.4) obtaining the purified product;
6) optionally, removing the water from the purified product, preferably removing the water from the purified product by lyophilization;
7) optionally, performing sub-packaging;
8) harvesting the product derived from *Rhodococcus ruber*; among them, steps 5.1), 5.2) and 5.3) can be performed in an interchangeable order or in parallel; step 6) and step 7) can be performed in an interchangeable order or in parallel.

Optionally, step 5) can further include a step of removing the cell membranes (for example, using a non-ionic surfactant).

Culture of *Rhodococcus ruber* is not limited to specific culture medium and culture parameters. The skilled person can use well-known and appropriate methods for culture, and can use petri dishes, culture flasks and fermenters according to the preparation scale.

For the disruption of *Rhodococcus ruber*, the purpose is to remove the intracellular substances, thus, ultrasonication, lysozyme and other technologies can be used. The skilled person understands that any known or future method suitable for disrupting gram-positive bacteria is suitable for the technical solution of the present disclosure.

The skilled person has the ability to adjust the specific parameters and equipments for culture, disruption, separation, collection, removal of impurity, and sub-packaging according to the subsequent application (such as oral administration, injection, external application, etc.) of the active ingredients (cell walls and components thereof), so as to avoid introducing factors that affect subsequent applications in the preparation steps.

In some embodiments, an organic solvent is used to remove lipids in the disrupted product. In some embodiments, a nuclease is used to remove DNAs and RNAs from the disrupted product. In some embodiments, a hydrolase is used to degrade proteins in the disrupted product. In some embodiments, a surfactant is used to remove the cell membrane from the disrupted product.

In some embodiments, the average particle size of disruption is 10 nm to 1000 nm; the follows may be mentioned: 10, 20, 30, 40, 50, 60, 70, 80, 90, 100, 110, 120, 130, 140, 150, 160, 170, 180, 190 nm±10 nm, and the ranges between any two of the above values. There are many methods for determining particle size (Hu Songqing et al., Modern technology of particle size measurement, Modern Chemical Industry, 2002, 22:1).

In some specific embodiments, the average particle size of disruption is 10 nm to 800 nm.

In some other specific embodiments, the average particle size of disruption is 10 nm to 500 nm.

In some other specific embodiments, the sub-packaging refers to sub-packaging into containers. The container is selected from the group consisting of bottle, tube, package, bag, plate, ampoule, injection device, aluminum film packaging, dressing and capsule.

For example, in specific embodiments, the sub-packaging refers to sub-packaging into bottles/ampoules. Solvent is added to the bottles/ampules just before use.

Specifically, in one aspect, the present invention provides use of an isolated *Rhodococcus ruber* cell wall skeleton in preparing a medicament for treating human papilloma virus infection, wherein:
preferably, said isolated *Rhodococcus ruber* cell wall skeleton is derived from *Rhodococcus ruber* deposited at China General Microbiological Culture Collection Center (CGMCC), No. 1-3 West Beichen Road, Chaoyang District, Beijing, on Mar. 22, 2019, under deposit number CGMCC 17431;

In preferred embodiments, said isolated *Rhodococcus ruber* cell wall skeleton is obtained by the following steps:
1) providing a *Rhodococcus ruber*;
2) culturing said *Rhodococcus ruber*;
3) collecting the cultured *Rhodococcus ruber*;
4) disrupting the cultured *Rhodococcus ruber* to obtain a disrupted product; and
5) removing lipids, nucleic acids and proteins from the obtained disrupt product.

In another aspect, the present invention provides use of a pharmaceutical composition in preparing a medicament for treating human papilloma virus infection, wherein, said pharmaceutical composition comprises:
an isolated *Rhodococcus ruber* cell wall skeleton, preferably, said isolated *Rhodococcus ruber* cell wall skeleton is derived from *Rhodococcus ruber* deposited at China General Microbiological Culture Collection Center (CGMCC), No. 1-3 West Beichen Road, Chaoyang District, Beijing, on Mar. 22, 2019, under deposit number CGMCC 17431; and
a pharmaceutically acceptable excipient;

preferably, said isolated *Rhodococcus ruber* cell wall skeleton is in 1 part by weight, and said pharmaceutically acceptable excipient is in 200 to 300 parts by weight;
preferably in 200, 210, 220, 230, 240, 250, 260, 270, 280, 290 or 300 parts by weight, or any point value within any two numerical ranges; preferably, said pharmaceutically acceptable excipient is selected from the group consisting of dextran, trehalose, glycine, xylitol, sodium carboxymethyl cellulose, erythritol, gelatin, magnesium stearate and mannitol.

In another aspect, the isolated *Rhodococcus ruber* cell wall skeleton provided by the present invention or the composition comprising the same can be used for topical administration; optionally, said topical administration can be subcutaneous or submucosal injection, or skin or mucosa coating.

Optionally, the isolated *Rhodococcus ruber* cell wall skeleton provided by the present invention or the composition comprising the same can be formulated as ointment, cream, plaster, gel, lotion, tincture, liniment, oil, paste, lyophilized powder, aerosol, suppository, patch or suspension; preferably, said medicament is formulated as a lyophilized powder formulation, and the lyophilized powder formulation is diluted in normal saline before use so that the *Rhodococcus ruber* cell wall skeleton is at a concentration of 15 µg/mL to 500 µg/mL, preferably at a concentration of 30 µg/mL to 240 µg/mL, more preferably at a concentration of 30 µg/mL to 120 µg/mL, more preferably at a concentration of 30 µg/mL to 60 µg/mL. In another aspect, the present invention provides use of an isolated *Rhodococcus ruber* cell wall skeleton in preparing a medical apparatus for treating human papilloma virus infection, wherein:
preferably, said isolated *Rhodococcus ruber* cell wall skeleton is derived from *Rhodococcus ruber* deposited at China General Microbiological Culture Collection Center (CGMCC), No. 1-3 West Beichen Road, Chaoyang District, Beijing, on Mar. 22, 2019, under deposit number CGMCC 17431;
said medical apparatus comprises said isolated *Rhodococcus ruber* cell wall skeleton, and
optionally, a pharmaceutically acceptable excipient;
optionally, said medical apparatus is an external medical apparatus, preferably selected from the following forms: dressing, patch, bandage or film; preferably, said dressing, patch, bandage or film is infiltrated with suspension of *Rhodococcus ruber* cell wall skeleton at a concentration of 15 µg/mL to 500 µg/mL, a concentration of 30 µg/mL to 240 µg/mL, more preferably a concentration of 30 µg/mL to 120 µg/mL, more preferably a concentration of 30 µg/mL to 60 µg/mL.

Specifically, the present invention provides use of the isolated *Rhodococcus ruber* cell wall skeleton according to the present invention and a pharmaceutical composition comprising the same in preparing a medicament for treating human papilloma virus infections of skin, cervix, vagina, labia, penis, anus, crissum, oropharynx, tonsil and oral cavity.

In another aspect, the present invention provides an isolated *Rhodococcus ruber* cell wall skeleton for use in treating human papilloma virus infection, wherein:
preferably, said isolated *Rhodococcus ruber* cell wall skeleton is derived from *Rhodococcus ruber* deposited at China General Microbiological Culture Collection Center (CGMCC), No. 1-3 West Beichen Road, Chaoyang District, Beijing, on Mar. 22, 2019, under deposit number CGMCC 17431.

In another aspect, the present invention provides a pharmaceutical composition for use in treating human papilloma virus infection, wherein, said pharmaceutical composition comprises:
an isolated *Rhodococcus ruber* cell wall skeleton, preferably, said isolated *Rhodococcus ruber* cell wall skeleton is derived from *Rhodococcus ruber* deposited at China General Microbiological Culture Collection Center (CGMCC), No. 1-3 West Beichen Road, Chaoyang District, Beijing, on Mar. 22, 2019, under deposit number CGMCC 17431; and
a pharmaceutically acceptable excipient;
preferably, said *Rhodococcus ruber* cell wall skeleton is in 1 part by weight, and said pharmaceutically acceptable excipient is in 200 to 300 parts by weight;
preferably, said *Rhodococcus ruber* cell wall skeleton is in 1 part by weight, and said pharmaceutically acceptable excipient is in 200, 210, 220, 230, 240, 250, 260, 270, 280, 290 or 300 parts by weight, or any point value within any two numerical ranges.

The isolated *Rhodococcus ruber* cell wall skeleton for use in treating human papilloma virus infection provided in the present invention is obtained by the following steps:
1) providing a *Rhodococcus ruber*;
2) culturing said *Rhodococcus ruber*;
3) collecting the cultured *Rhodococcus ruber*;
4) disrupting the cultured *Rhodococcus ruber* to obtain a disrupted product; and
5) removing lipids, nucleic acids and proteins from the obtained disrupted product.

In another aspect, the present invention provides a method for the treatment of human papilloma virus infection, said method comprising administration of a therapeutically effective amount of an isolated *Rhodococcus ruber* cell wall skeleton or a pharmaceutical composition comprising said isolated *Rhodococcus ruber* cell wall skeleton to a subject in need, wherein:
preferably, said isolated *Rhodococcus ruber* cell wall skeleton is derived from *Rhodococcus ruber* deposited at China General Microbiological Culture Collection Center (CGMCC), No. 1-3 West Beichen Road, Chaoyang District, Beijing, on Mar. 22, 2019, under deposit number CGMCC 17431; preferably, said administration is topical administration; preferably, said topical administration is skin or mucosa coating, or subcutaneous or submucosal injection;
preferably, said therapeutically effective amount is at a unit dose of 1 µg to 1000 µg; preferably 15 µg to 500 µg, preferably 30 µs to 240 µg, more preferably 30 µg to 120 µg, more preferably 30 µg to 60 µg;
preferably, said treatment is performed at a frequency selected from the group consisting of: administering 1 to 3 times a day, 1 to 6 times two days, 1 to 9 times three days, 1 to 14 times a week, 1 to 60 times a month; more preferably administering once a day;
preferably, said treatment lasts from 2 days to 2 months, more preferably lasts for 1 week, 2 weeks, 3 weeks, 4 weeks, 5 weeks, 6 weeks, 7 weeks or 8 weeks.

In the context of the present application, the only therapeutic (or preventive) active ingredient in the medicament or the pharmaceutical composition is the product derived from *Rhodococcus ruber*, notably the product comprising *Rhodococcus ruber* components (such as proteins, nucleic acids, lipids, cell walls and components thereof, carbohydrates and metabolites), specifically, the product comprising *Rhodococcus ruber* cell wall (more preferably *Rhodococcus ruber* cell wall skeleton or composition thereof).

BRIEF DESCRIPTION OF THE DRAWINGS

FIG. 1: The colony morphology of *Rhodococcus ruber*.
FIG. 2: The identification results of 16S rRNA.

DETAILED DESCRIPTION OF THE INVENTION

"Isolation" refers to the separation of the *Rhodococcus ruber* of the present disclosure from its original growth environment.

The skilled person knows that the cell wall structures of gram-positive bacteria and gram-negative bacteria are different. Specifically, the cell wall of gram-positive bacteria is thicker (usually 20 nm to 80 nm), comprising about 90% peptidoglycan and about 10% teichoic acid (a polymer formed by alcohol and phosphoric acid molecules, usually existing in the form of sugar ester or amino acid ester). The peptidoglycan layer is dense, even as many as 20 layers. However, the cell wall of gram-negative bacteria is much thinner than that of gram-positive bacteria, and the structure is more complex, divided into outer membrane and peptidoglycan layer (usually 2 nm to 3 nm).

The peptidoglycan layer is a unique component of the bacterial cell wall and is a derivative of heteropolysaccharide. Each peptidoglycan monomer comprises 3 parts: the sugar unit (for example, at least two sugar molecules are connected by glycosidic bonds to form the framework of peptidoglycan), the peptide tail (a short peptide chain formed by linking several amino acids, which is connected to a N-acetylmuramic acid molecule), and the peptide bridge (which crosslinks the adjacent "peptide tails" to form a high-strength network structure). Different bacteria have different peptide bridges, peptide tails and cross-linking manners.

Isolated *Rhodococcus ruber* Cell Wall Skeleton

In the present disclosure, "isolated *Rhodococcus ruber* cell wall" can be understood as either a complete cell wall or an incomplete cell wall (for example, disrupted or partially degraded). Under the instruction of the present disclosure, the skilled person will understand that the ingredients exhibiting the desired activity are derived from *Rhodococcus ruber* cell wall (for example, the cell wall itself or composition thereof). Therefore, various forms are allowed to be used in clinical applications, including complete cell walls, disrupted cell walls, incompletely degraded products of cell walls, cell wall components, cell wall extracts, etc., which are all included in the scope of the present disclosure.

Cell Wall Skeleton

A component that constitute the main structure of the cell wall; however, it cannot be understood as merely representing the cross-linked network-like entity in the cell wall, and the skilled person understands that other cell wall compositions adsorbed by, bound to, or carried by the cross-linked network-like entity cannot be excluded.

*Rhodococcus ruber*

The *Rhodococcus ruber* used in the embodiments of the present disclosure refers to the *Rhodococcus ruber* species of the *Rhodococcus* genus, and is not limited to a specific cell strain.

Non-limiting examples include the TOY7 strain (Agricultural Environment Microbiological Culture Collection, Nanjing Agricultural University), CGMCC No. 4795, DSM43338, CCTCC No. 2012035, CGMCC No. 16640 and CGMCC 17431.

Identification of *Rhodococcus ruber*

According to the known or future microbial identification techniques, the skilled person can perform taxonomic identification on a strain of bacteria. For example, the available identification techniques include morphology, physiological and biochemical characteristics, 16S rRNA, and the like. The skilled person understands that with the development of science and technology, identification techniques involve different methods. In the earlier period, morphological and biochemical identification methods were mainly used, but the reliability of these methods is not high. After the advent of sequencing technology, the skilled person can identify bacteria strains in a more reliable way. For example, when the DNA sequences of 16S rRNA are identified as having more than 97% (inclusive) of identity, it is determined that the two bacteria belong to the same species (Hua Gougen et al., The taxonomy and application of *Rhodococcus*, Microbiology China, 2003: 30 (4)). In terms of *Rhodococcus ruber*, the known strains deposited in international (or national) culture collection units are used as model strains, and are compared with the strain to be identified.

Dosage Form

The medicament or pharmaceutical composition or active ingredient or product of the present disclosure can be embodied in, but not limited to, the following forms: ointment, cream, plaster, gel, lotion, tincture, liniment, oil, paste, lyophilized powder, aerosol, suppository, patch, suspension, oral liquid, buccal tablet and skin care product (cleanser, toning lotion, essence, lotion, cream and mask).

Excipient

An excipient suitable for the present disclosure is for example, but not limited to: dextran, lactose, microcrystalline cellulose, trehalose, glycine, xylitol, sodium carboxymethyl cellulose, erythritol, gelatin, magnesium stearate, mannitol, propellant, humectant, solvent, solubilizer, emulsifier, antioxidant, pH regulator and preservative. Specifically, non-limiting examples also include: white vaseline, carbomer, hydroxypropyl methylcellulose, methyl cellulose, sodium hydroxymethyl cellulose, chitosan, sucralfate chitosan, polyvinylpyrrolidone, polyvinyl alcohol, sodium hyaluronate, dimethyl ether, tetrafluoroethane, hydrofluoroalkane, glycerin, propylene glycol, deionized water, water for injection, distilled water, ethanol, hexadecanol, octadecanol, p-aminobenzoic acid, acetamide, isopropanol, Tween, polyoxyethyl hydrogenated castor oil, stearic acid, glyceryl monostearate, triglycerol monostearate, sucrose fatty acid ester, sucrose ester, sucrose acetate isobutyrate, sorbitan tristearate, isopropyl myristate, cholesterol, squalene, squalane, n-butanol, ethylene glycol, ethanol, propylene glycol, polyglycerol ester, sulfite, cysteine, di-tert-butyl hydroxytoluene, potassium sorbate, phosphate buffer solution, triethanolamine, sodium hydroxide, ethylenediamine, laurylamine, sodium bicarbonate, hydrochloric acid, nipagin, thimerosal, chlorocresol, trichlorobutanol, benzoic acid and sodium salt thereof.

Preparation Unit

The medicament or pharmaceutical composition or active ingredient or product of the present disclosure can be prepared in the form of a unit preparation (unit form).

In some embodiments, the medicament (or preparation, or therapeutic agent, or medical apparatus) comprises a unit dose of:

0.001 mg to 500 mg of the product derived from *Rhodococcus ruber*; or 0.001 mg to 500 mg of the *Rhodococcus ruber* cell wall; or 0.001 mg to 500 mg of the *Rhodococcus ruber* cell wall skeleton.

Specific example of the unit dose is 0.001, 0.005, 0.01, 0.05, 0.1, 0.2, 0.3, 0.4, 0.5, 0.6, 0.7, 0.8, 0.9, 1, 2, 5, 10, 15, 20, 25, 30, 40, 50, 60, 70, 80, 90, 100, 150, 200, 250, 300, 350, 400, 450, 500 mg±10%, or the range between any two of the above values.

"Administering", "giving", "providing to" and "treating", when applied to animals, humans, cells, tissues, organs or biological samples, refer to the contact of the medicament (therapeutic agent, active ingredient or composition) with the animals, humans, cells, tissues, organs or biological samples.

"Treatment" means administering an internal or external medicament (therapeutic agent, active ingredient or composition) (such as the *Rhodococcus ruber* cell wall or pharmaceutical composition thereof according to the present disclosure) to a subject, for alleviating (relieving, delaying, improving, curing) one or more disease symptoms to a clinically measurable degree in the subject (or population) treated, wherein the subject has, is suspected of having, or is susceptible to one or more diseases or symptoms thereof.

The amount of the medicament (therapeutic agent, active ingredient or composition) that effectively alleviates any disease symptom is called a therapeutically effective amount. It can vary depending on a variety of factors, such as the disease state, age and body weight of the subject. It should be understood that the medicament (therapeutic agent, active ingredient or composition) may be ineffective in alleviating the target disease or symptoms thereof in a single subject, but it can be determined according to any statistical test method known in the art (such as Student's t test, chi-square test and U test according to Mann and Whitney) that, the medicament (therapeutic agent, active ingredient or composition) is statistically effective for the target disease or symptoms thereof.

"Optionally" means that what is described later can happen, but does not have to happen; it depends on the situation. For example, "optionally, performing sub-packaging" means that the product is allowed to be sub-packaged, but it is not required to be sub-packaged; whether the product is sub-packaged or not does not affect the achievement of the technical effects.

"A", "an", "single" and "the", if not explicitly stated, also include plural forms.

The present disclosure is further described below with reference to the examples, preparation examples and test examples. However, these examples, preparation examples and test examples do not limit the scope of the present disclosure. When the specific conditions are not specified, operation should be done in accordance with the normal conditions and the conditions recommended by the raw material supplier. The reagents for which the sources are not specifically indicated are conventional reagents purchased on the market.

The skilled person especially understands that although a specific cell line is used in the following specific examples, the achievement of the technical effects is not limited to the specific cell line, and any species belonging to the *Rhodococcus* genus, *Rhodococcus ruber* species is applicable.

EXAMPLES

Example 1. Deposit of the Strain

The inventors deposited the laboratory-preserved master strain at China General Microbiological Culture Collection Center (CGMCC), No. 1-3 West Beichen Road, Chaoyang District, Beijing, on Mar. 22, 2019, under deposit number CGMCC 17431. Tests showed that the deposited strain is viable.

Example 2. Identification of the Strain

1. Morphological Characteristics of the Colony Observed by the Naked Eyes

The strain was cultured on a glycerol agar medium at 30 to 37° C. (specifically at 32 to 35° C.) for 12 to 72 (specifically 36 to 60, such as 40 to 50) hours, and the colonies were observed (FIG. 1):
  swelled up;
  in orange-red color (slightly different depending on influences of light, the color of the culture medium, etc.);
  with a dry and wrinkled surface, slightly shiny (slightly different depending on differences in culture conditions);
  fragile to the touch;
  with a colony size of about 1 mm to 2 mm (slightly different depending on differences in culture conditions).

2. Observation Under Microscope
  The bacteria were branched and had diaphragms, to form mycelium (slightly different depending on differences in culture conditions);
  The hyphae were divided to form regular short and thick cells (slightly different depending on differences in culture conditions);
  After culturing for 4 to 5 days, the bacteria became short rod-shaped or spherical (slightly different depending on differences in culture conditions).

3. Staining Property
  The strain was gram stain positive.

4. Biochemical Reactions
  The strain was cultured on a glycerol agar slant medium at 30 to 37° C. (specifically at 32 to 35° C.) for 12 to 72 (specifically 36 to 60, such as 40 to 50) hours. Then, the following tests were performed on the culture.

4.1 Acid Production from Carbohydrates:
  Positive: glycerin, mannitol, sorbitol, D-arabitol, D-fructose and D-glucose;
  Negative: inositol, inulin, lactose, sucrose, starch, maltose, glycogen, xylitol, gluconate, trehalose, erythritol, melezitose, melibiose, raffinose, cellobiose, amygdalin, gentiobiose, adonol, arbutin, D-arabinose, L-arabinose, α-methyl-D-glucoside, α-methyl-D-mannoside, D-ribose, D-xylose, L-xylose, N-acetyl-glucosamine, D-turanose, D-lyxose, β-methyl-D-xyloside, D-galactose, D-tagatose, D-fucose, L-fucose, D-mannose, L-sorbose, L-arabinitol, L-rhamnose and 2-keto-gluconate.

4.2 Enzyme Activity Assay (API ZYM):
  Positive: alkaline phosphatase, lipoid esterase (C8), lipase (C14), leucine arylaminase, valine arylaminase, cystine arylaminase, trypsin, chymotrypsin, acid phosphatase, naphthol-AS-B1-phosphohydrolase and α-glucosidase;
  Negative: N-acetyl-glucosaminidase, esterase (C4), β-galactosidase, β-uronidase, β-glucosidase, α-galactosidase, α-mannosidase and β-fucosidase.

4.3 Nitrate reduction reaction: positive; catalase: positive; tyrosinase: positive; amylase: negative; oxidase: negative; gelatin liquefaction: negative.

4.4 Sole Carbon Source:
Biolog Gen II Growth Experiment:
  Positive for glucuronamide, β-hydroxy-DL butyric acid, D-fructose-6-phosphate, α-D-glucose, D-fructose, D-mannitol, D-arabitol, D-sorbitol, quinic acid, γ-aminobutyric acid, citric acid, L-malic acid, bromosuccinic acid, Tween 40, propionic acid and acetic acid;

Biolog Gen III Chemical Sensitivity Experiment

Sensitive to p-dimethylamine tetracycline, sodium tetradecyl sulfate, rifamycin SV, pH 5.0, 8% sodium chloride, lincomycin, fusidic acid, D-serine, vancomycin, tetrazolium violet and tetrazolium blue;

Insensitive to sodium bromate, 1% sodium lactate, pH 6.0, 1%-4% sodium chloride, nalidixic acid, lithium chloride, potassium tellurite, aztreonam and sodium butyrate.

4.5. 16S rRNA Identification

The 15 strains isolated from the working seed tube and the 10 different strains isolated from the original seed tube were subjected to genome extraction, 16S rRNA amplification and sequencing. The 16S rRNA genes of the total of 25 strains have 100% identity. This means that the 25 strains are of the same species (FIG. 2).

At the same time, the neighbor-joining strain phylogenetic tree constructed based on the Kimura2-parameter algorithm showed that the strain was classified as *Rhodococcus ruber*.

Preparation Examples

Preparation Example 1. Culture Methods

1. The *Rhodococcus ruber* with the deposit number CGMCC 17431 can be cultured by conventional microbial production methods.
2. The culture method can be solid culture or liquid culture.
3. The nutrient sources in the culture medium are no specifically indicated. The culture medium can contain carbon sources, nitrogen sources and other nutrient sources that are commonly used for microbial culture.

The carbon source can be any carbon source that can be used by *Rhodococcus ruber*, for example, fructose, glucose, and the like.

The nitrogen source can be meat extract, peptone, ammonium salt, nitrate and other organic or inorganic nitrogen-containing compounds.

For other nutrient sources, some inorganic salts can be added appropriately, for example, NaCl and phosphates.

4. The culture conditions (temperature, time, etc.) are not strictly limited. The skilled person can choose the conditions that maximize the yield based on the preliminary small-scale pilot test data.
5. As an example, the following culture condition was used to ferment *Rhodococcus ruber*:

(1) The Medium Composition Included:

Peptone, beef extract, sodium chloride, phosphate, glycerin (and, optionally agar, when in solid culture).

(2) Parameters of the Culture Method:

After the working strain was recovered, it was transferred to a solid culture medium for 3-5 days, and then transferred to liquid culture (30-37° C., maintained for 3-5 days). The fed-batch semi-continuous mode or the batch mode can be used. The pH, bacterial density, dissolved oxygen and carbon source consumption were monitored during culture.

Preparation Example 2. Bacteria Disruption

The bacteria obtained in Preparation Example 1 were collected and the cells were disrupted (for example, but not limited to sonication). Any appropriate well-known method in the art was also allowed to be used for bacteria disruption, such as CN101250490A or CN101323865A.

The disruption state was checked under a microscope. There should be no more than 5 intact bacteria visible in each visual field. The disruption was considered as qualified when several (10 to 30) visual fields checked met this standard.

Preparation Example 3. Removal of Nucleic Acids, Lipids, Proteins and Cell Membranes 1. Removal of Nucleic Acids:

The supernatant after disruption was centrifuged. DNase and RNase were added to the obtained precipitate, and nucleic acids were removed according to the operation recommended by the supplier of the enzymes.

2. Removal of Proteins:

Common protease (such as trypsin) was added to the precipitate, and proteins were removed according to the operation recommended by the supplier of the enzyme.

3. Removal of Lipids:

Organic reagents (for example, but not limited to, one of acetone, ether and ethanol or the combination thereof) were added to the precipitate, and lipids were removed according to conventional operations in the art.

4. Removal of Cell Membranes:

Triton X-100 was added to the precipitate, and the precipitate was collected by centrifugation according to conventional operations in the art, and rinsed with PBS.

It should be understood that the skilled person can adjust the orders of the above steps of removing impurities to make them compatible. After removing the non-cell wall components, the precipitate was reconstituted in water for injection for later use. Optionally, it could be sterilized at 115° C. for 20-30 minutes as a stock solution of the cell wall skeleton (mainly comprising the cell wall skeleton and components thereof).

5. Yield

A total of 653 mL of bacterial liquid (after disruption) was collected from 159 Kolle flasks. The wet weight yield was 138 g; the cell wall skeleton yield was about 0.87 g/Kolle flask.

Preparation Example 4. Preparation Methods of the Pharmaceutical Compositions

1. Excipients (such as dextran 40, mannitol or trehalose) were added to the product obtained in Preparation Example 3, filled into a vial to result in the pharmaceutical composition.

TABLE 1

The pharmaceutical composition can be formulated in various forms

| Composition | Capacity of each vial | Component and amount | |
|---|---|---|---|
| Composition 1 | 2 mL | Active ingredient | 60 μg |
| | | Dextran 40 | 15 mg |
| Composition 2 | 2 mL | Active ingredient | 240 μg |
| | | Dextran 40 | 48 mg |
| Composition 3 | 2 mL | Active ingredient | 120 μg |
| | | Dextran 40 | 36 mg |
| Composition 4 | 2 mL | Active ingredient | 60 μg |
| | | Trehalose | 12 mg |
| Composition 5 | 2 mL | Active ingredient | 120 μg |
| | | Trehalose | 36 mg |
| Composition 6 | 2 mL | Active ingredient | 120 μg |
| | | Mannitol | 36 mg |

TABLE 1-continued

The pharmaceutical composition can be formulated in various forms

| Composition | Capacity of each vial | Component and amount | |
|---|---|---|---|
| Composition 7 | 2 mL | Active ingredient | 60 μg |
| | | Mannitol | 12 mg |

2. The product obtained in Preparation Example 3 (active ingredient 30 μg to 120 μg) was coated on the dressing to prepare medical apparatus for external use.
3. The pharmaceutical compositions in Table 1 were lyophilized to prepare lyophilized powders (numbered as compositions 1 to 7, respectively).
4. Quality inspection (composition 1 was taken as an example)

TABLE 2

| Quality inspection items | |
|---|---|
| Appearance | White unconsolidated solid or powder |
| Water content | ≤6% |
| Solubility | Qualified if it was dissolved within 1 minute after 2.0 mL of NaCl injection was added; |
| Identification of sugars | The solution was blue-green in color |
| Content of muramic acid | 2.0 μg/vial (criteria: ≥1.0 μg/vial) |
| Amount of residual proteins | 0.4 μg/vial (criteria: ≤9.0 μg/vial) |
| Amount of residual RNAs | 0.8% (criteria: no more than 5%) |
| Amount of residual DNAs | 0.9% (criteria: no more than 5%) |
| Amount of residual Triton X-100 | Undetected (criteria: no more than 5%) |
| Amount of residual lipids | 3.8% (criteria: no more than 5%) |
| Phagocytosis rate | 75% (criteria: ≥40%) |
| Phagocytic index | 1.05 (criteria: ≥0.50) |
| Abnormal toxicity in mice | The composition was considered as qualified if all the mice were alive and had no abnormal reactions during the observation period, and the body weight of each mouse was increased at the end of the inspection. |
| Abnormal toxicity in guinea pigs | The composition was considered as qualified if all the guinea pigs were alive and had no abnormal reactions during the observation period, and the body weight of each guinea pig was increased at the end of the inspection. |

Test Examples

Test Example 1. Pharmacological Tests

1. After intravenous injection of each composition at the doses 20, 40 and 80 times higher than the human clinical dose, the blood pressure, respiration, heart rate and electrocardiogram of the anesthetized cats were monitored, and the compositions had no significant effect;
2. After intravenous injection of each composition at the dose 1000 times higher than the human clinical dose, the compositions had no significant effect on the coordinated movement and learning and memory function of mice.

It can be seen that the pharmaceutical compositions of the present invention (composition 1 to composition 7) have no significant effect on the mental state, nervous system, cardiovascular system and respiratory system of animals.

Test Example 2. Safety Tests

1. Sterility Test:
The results were negative, proving the sterility of the compositions.
2. Acute Toxicity Test in Mice:
The compositions were administered to the experimental groups by subcutaneous injection and intraperitoneal injection, and the dose was 5 times higher than the dose used for human. The control group was treated with sterile normal saline 0.5 mL/animal. The animals were continuously observed for 7 to 8 days. The mice were in good condition and had no abnormality in their body weight or their organs.
3. Long-Term Toxicity Test:

The compositions were vaginally administered at the dose 30 times higher than that for clinical use once a day continuously for three months. No toxic effects were found in dogs; the electrocardiograms and blood biochemical indicators were within the normal range. After stopping the administration for two weeks, no delayed toxicity was observed (composition 1 to composition 7).

Test Example 3. Stability Tests

The pharmaceutical compositions were placed at room temperature (18-25° C.) for 0, 1, 2, 3, 8, 14 and 21 months, and the alanine content, muramic acid content, phagocytosis rate and phagocytic index had no statistically significant difference compared to those at the start of the test (three batches were tested).

In summary, the lyophilized powder formulation of the pharmaceutical composition can be stored stably for 24 months (composition 1 to composition 7).

Test Example 4. Phagocytosis Tests

Macrophages are the main cells of the mononuclear phagocyte system. The activation of phagocytes after antigen stimulation can significantly enhance the phagocytic function. After inducing the production of peritoneal macrophages in the mice, the mice were intraperitoneally injected with chicken red blood cells. After 30 minutes, the mice were sacrificed and the peritoneal fluid was taken out and stained. The percentage of the phagocytized red blood cells was counted under a microscope to determine the killing ability of the phagocytes, indirectly measuring the non-specific immunity level of the body.

Composition 1 of the present application was used for testing. For composition 1, the phagocytosis rate was 75% and the phagocytic index was 1.05. While, the phagocytosis rate and phagocytic index for the negative control (excipient) and blank control (normal saline) were all relatively low. These results show that the cell wall skeleton of the present application has a strong ability to promote immunophagocytosis.

Effect Example: Use of the *Rhodococcus ruber* Cell Wall Product of the Present Invention in the Treatment of HPV Infected Subjects In view of the immunophagocytosis-promoting ability of the *Rhodococcus ruber* cell wall skeleton of the present invention discovered by the inventors, the inventors used the following methods to identify the effect of the *Rhodococcus ruber* cell wall product obtained by the method of the present invention on the treatment of human papilloma virus (HPV) infection.

It is known that the HPV detection methods in the art usually include the following:
1. Cytological Smear Testing:
It was usually named as the Papanicolaou staining detection method in the past, also known as the smear detection method. In the method, the collected cervical secretions are smeared on glass slides and observed under a microscope, mainly to check whether there are vacuolar cells or keratinocytes. The detection rate is 70-76%.
2. Thin-Prep Liquid Based Cytology Test (TCT):
Samples are collected at the cervix using special brushes. Then the impurities in the collected samples are separated using the cell preservation solution to form an ultra-thin clear cell smear, which can detect the presence of HPV virus and determine the type of the virus. The method is also known as TCT. The detection rate is 70-95%.
3. Immunohistochemical Detection Methods:
After immunizing the animal with HPV, the polyclonal antibody produced is used to check the tissue HPV antigen, and the PAP method is used to display the virus protein to prove the presence of the virus antigen. When HPV protein is positive, light red color appeared in epithelial cells is considered as weak positive reaction, and brown granular sedimentation observed in the vacuole cell nucleus is considered as positive. But the detection rate is low (40-60%), the sensitivity is not high, and the type of the virus cannot be determined.
4. HPV DNA Detection Methods:
(1) Polymerase Chain Reaction (PCR):
Secretions are collected from the vagina and external cervical orifice using wipers or cotton swabs soaked in normal saline. HPV DNA is extracted by centrifugation, washing and other methods, and then PCR amplification and gel electrophoresis are performed. Diagnosis can be made according to observation of the electrophoresis and sample comparison. Although this method is simple, it cannot locate the virus or determine whether the virus is dead or alive.
(2) DNA Hybridization Method (Using PCK):
HPV DNA molecular hybridization technology and CP-14 immune hybridization method are applied. The sample is considered as positive when more than 3 fluorescent spots can be seen under a fluorescence microscope at 400×. The virus can be typed, the HPV-DNA sequence can be detected by nucleic acid hybridization, and specific HPV-DNA amplification zone can be seen by PCR detection. However, this method is cumbersome and expensive. Certain equipment and conditions are required.

The inventors used the lyophilized powder formulation of composition 1 prepared in Table 1 of the present invention, which was diluted with normal saline to 30 µg/mL or 60 µg/mL before use. Use of the composition of the present invention containing *Rhodococcus ruber* cell wall components in the treatment of cervical HPV infection was discussed by cervical local injection or external cervical application in subjects with cervical HPV infection.

The above-mentioned cytological smear testing and TCT method were used to diagnose HPV infected patients. After signing the "informed consent", the patients were treated by external application or local injection of the composition of the present invention at the infected site.

The comprehensive treatment method was to administer the composition of the present invention once a day, for 20 days as a treatment cycle. The administration should be stopped during the menstrual period of the women.

Results

| Patient | Age | Active ingredient concentration | HPV type before treatment | Route of administration | Frequency of treatment | HPV type after 20 days of treatment |
| --- | --- | --- | --- | --- | --- | --- |
| 1 | 39 | 30 µg/ml | 16 | Cervical external application | Once every two days | Negative |
| 2 | 49 | 30 µg/ml | 52, 44 | Cervical external application | Once every two days | Negative |
| 3 | 50 | 30 µg/ml | 51 | Cervical external application | Once every two days | Negative |
| 4 | 57 | 30 µg/ml | 59 | Cervical external application | Once every two days | Negative |
| 5 | 30 | 30 µg/ml | 52 | Cervical external application | Once every two days | Negative |
| 6 | 33 | 30 µg/ml | 52, 66 | Cervical external application | Once every two days | Negative |
| 7 | 35 | 30 µg/ml | 16, 58 | Cervical external application | Once every two days | Negative |
| 8 | 41 | 30 µg/ml | 58, 84 | Cervical external application | Once every two days | Negative |
| 9 | 43 | 30 µg/ml | 18, 11 | Cervical external application | Once every two days | Negative |
| 10 | 60 | 30 µg/ml | 16 | Cervical external application | Once every two days | Negative |
| 11 | 34 | 30 µg/ml | 16 | Cervical external application | Once every two days | Negative |
| 12 | 48 | 30 µg/ml | 52 | Cervical external application | Once every two days | Negative |

| Patient | Age | Active ingredient concentration | HPV type before treatment | Route of administration | Frequency of treatment | HPV type after 20 days of treatment |
|---|---|---|---|---|---|---|
| 13 | 30 | 30 μg/ml | 68 | Cervical external application | Once every two days | Negative |
| 14 | 53 | 30 μg/ml | 18, 31 | Cervical external application | Once every two days | Negative |
| 15 | 33 | 60 μg/ml | 16 | Cervical external application | Once every two days | Negative |
| 16 | 48 | 60 μg/ml | 51, 52 | Cervical external application | Once every two days | Negative |
| 17 | 31 | 60 μg/ml | 16, 45 | Cervical injection | Once every two days | Negative |
| 18 | 37 | 60 μg/ml | 52 | Cervical injection | Once every two days | Negative |
| 19 | 30 | 60 μg/ml | 58 | Cervical injection | Once every two days | Negative |
| 20 | 32 | 60 μg/ml | 58 | Cervical injection | Once every two days | Negative |
| 21 | 29 | 60 μg/ml | 16 | Cervical injection | Once every two days | Negative |
| 22 | 37 | 60 μg/ml | 51 | Cervical injection | Once every two days | Negative |
| 23 | 29 | 60 μg/ml | 66 | Cervical injection | Once every two days | Negative |
| 24 | 37 | 60 μg/ml | 16, 18 | Cervical injection | Once every two days | Negative |
| 25 | 35 | 60 μg/ml | 58 | Cervical injection | Once every two days | Negative |

During the experiment, the control group of 5 patients was treated with cervical external application or injection of dextran 40 solution without active ingredients in parallel. There was no conversion in HPV positivity before and after treatment.

From the above results, it can be seen that the diluted preparation comprising the *Rhodococcus ruber* cell wall skeleton of the present invention can effectively treat human cervical HPV infection, and the negative conversion ratio of the virus reaches 100%.

What is claimed is:

1. A method for the treatment of human papilloma virus infection, said method comprising administration of a therapeutically effective amount of an isolated *Rhodococcus ruber* cell wall skeleton or a pharmaceutical composition comprising said isolated *Rhodococcus ruber* cell wall skeleton to a subject in need, wherein:
    said isolated *Rhodococcus ruber* cell wall skeleton is derived from *Rhodococcus ruber* deposited at China General Microbiological Culture Collection Center, No. 1-3 West Beichen Road, Chaoyang District, Beijing, on Mar. 22, 2019, under deposit number CGMCC 17431.

2. The method according to claim 1, wherein said therapeutically effective amount is at a unit dose of 1 μg to 1000 μg.

3. The method according to claim 2, wherein said therapeutically effective amount is at a unit dose of 15 μg to 500 μg.

4. The method according to claim 3, wherein said therapeutically effective amount is at a unit dose of 30 g to 60 g.

5. The method according to claim 1, wherein said isolated *Rhodococcus ruber* cell wall skeleton is obtained by the following steps:
    a) providing *Rhodococcus ruber* CGMCC 17431;
    b) culturing said *Rhodococcus ruber*;
    c) collecting the cultured *Rhodococcus ruber*;
    d) disrupting the collected *Rhodococcus ruber* to obtain a disrupted product; and
    e) removing lipids, nucleic acids and proteins from the obtained disrupted product.

6. The method according to claim 1, wherein said treatment is performed at a frequency selected from the group consisting of: administering 1 to 3 times a day, 1 to 6 times per two days, 1 to 9 times per three days, 1 to 14 times a week, and 1 to 60 times a month.

7. The method according to claim 1, wherein said treatment lasts between 2 days and 2 months.

8. The method of claim 1, wherein said administration is topical administration.

9. The method of claim 8, wherein said topical administration is skin or mucosa coating, or subcutaneous or submucosal injection.

\* \* \* \* \*

UNITED STATES PATENT AND TRADEMARK OFFICE
CERTIFICATE OF CORRECTION

PATENT NO. : 12,097,224 B2  
APPLICATION NO. : 17/421718  
DATED : September 24, 2024  
INVENTOR(S) : Bo Gai et al.

Page 1 of 1

It is certified that error appears in the above-identified patent and that said Letters Patent is hereby corrected as shown below:

On the Title Page

Item (54) and in the Specification, Column 1, Lines 1-4, within the title, "USE OF CELL WALL SKELETON OF ISOLATED RHODOCOCCUS RUBER FOR PREPARING HUMAN PAPILLOMA VIRUS INFECTION TREATMENT DRUG" should read --USE OF CELL WALL SKELETON OF ISOLATED RHODOCOCCUS RUBER FOR PREPARING HUMAN PAPILLOMAVIRUS INFECTION TREATMENT DRUG--.

In the Claims

In Claim 4, Column 20, Line 33, "30 g to 60 g" should read --30 μg to 60 μg--.

Signed and Sealed this
First Day of April, 2025

Coke Morgan Stewart
*Acting Director of the United States Patent and Trademark Office*